United States Patent
Hefetz et al.

(10) Patent No.: US 9,737,278 B2
(45) Date of Patent: Aug. 22, 2017

(54) METHODS AND SYSTEMS FOR MULTI-WINDOW IMAGING

(71) Applicant: General Electric Company, Schenectady, NY (US)

(72) Inventors: Yaron Hefetz, Alonim (IL); Avi Bar-Shalev, Kiryat Hayim (IL)

(73) Assignee: General Electric Company, Schenectady, NY (US)

( * ) Notice: Subject to any disclaimer, the term of this patent is extended or adjusted under 35 U.S.C. 154(b) by 22 days.

(21) Appl. No.: 14/870,310

(22) Filed: Sep. 30, 2015

(65) Prior Publication Data

US 2017/0086768 A1    Mar. 30, 2017

(51) Int. Cl.
| | |
|---|---|
| G06K 9/00 | (2006.01) |
| A61B 6/00 | (2006.01) |
| G06T 7/00 | (2017.01) |
| G06T 5/00 | (2006.01) |
| G06T 11/00 | (2006.01) |
| A61B 6/03 | (2006.01) |
| G06K 9/34 | (2006.01) |

(52) U.S. Cl.
CPC ........... *A61B 6/5241* (2013.01); *A61B 6/032* (2013.01); *A61B 6/461* (2013.01); *G06T 5/009* (2013.01); *G06T 7/0083* (2013.01); *G06T 11/006* (2013.01); *G06T 11/008* (2013.01); *G06T 2207/10081* (2013.01); *G06T 2207/20092* (2013.01); *G06T 2207/20208* (2013.01); *G06T 2207/20221* (2013.01); *G06T 2211/421* (2013.01); *G06T 2211/424* (2013.01)

(58) Field of Classification Search
CPC .................................. G06K 9/00; G06T 7/00
USPC .... 382/128–134, 164, 171, 177, 179; 378/4, 378/8, 21–27, 901; 600/141, 516
See application file for complete search history.

(56) References Cited

U.S. PATENT DOCUMENTS

| | | | | |
|---|---|---|---|---|
| 7,385,200 | B2 * | 6/2008 | Vija | .................... G06T 11/005 |
| | | | | 250/363.04 |
| 9,087,259 | B2 | 7/2015 | Pekar et al. | |
| 2012/0308107 | A1 * | 12/2012 | Engel | .................... A61B 6/025 |
| | | | | 382/131 |
| 2013/0034203 | A1 * | 2/2013 | Wang | .................... A61B 6/03 |
| | | | | 378/41 |

OTHER PUBLICATIONS

Prokop, M. et al., "Spiral and Multislice Computed Tomography of the Body," (Excerpt From), Jan. 18, 2002, 6 pages.
Seeram. E., "Computed Tomography: Physical Principles, Clinical Applications, and Quality Control," (Excerpt From), Third Edition, Nov. 13, 2008, 6 pages.

* cited by examiner

*Primary Examiner* — Abolfazl Tabatabai
(74) *Attorney, Agent, or Firm* — McCoy Russell LLP

(57) ABSTRACT

Methods and systems are provided for multi-window imaging. In one embodiment, a method comprises segmenting an image reconstructed from acquired projection data into segments, converting pixel values based on a mapping for each segment to generate converted segments, and outputting, to a display device, a composite image comprising a combination of the converted segments. The composite image includes a border delineating the converted segments. In this way, multiple windows collectively covering a large dynamic range may be combined into a single image.

20 Claims, 7 Drawing Sheets

METHODS AND SYSTEMS FOR MULTI-WINDOW IMAGING

FIELD

Embodiments of the subject matter disclosed herein relate to non-invasive diagnostic imaging, and more particularly, to multi-window imaging.

BACKGROUND

Non-invasive imaging technologies allow images of the internal structures of a patient or object to be obtained without performing an invasive procedure on the patient or object. In particular, technologies such as computed tomography (CT) use various physical principals, such as the differential transmission of x-rays through the target volume, to acquire image data and to construct tomographic images (e.g., three-dimensional representations of the interior of the human body or of other imaged structures).

The radio density (also referred to as the CT attenuation or the CT number), of each voxel of the image data is represented by a numeric value along an arbitrary scale, the Hounsfield scale, which may be defined so that −1000 represents the radio density of air and +1000 represents the radio density of bone. Air causes very little x-ray attenuation and is typically depicted in black on x-ray films, in CT images, and so on, whereas bone greatly attenuates x-rays and is typically depicted in white on these films and images. Fat has a radio density of about −120 Hounsfield units (HU), and muscle has a radio density of about +40 HU. Water is defined as having a radio density of 0 HU.

Intermediate amounts of CT attenuation are usually depicted by shades of gray in CT images. Because the human eye is unable to distinguish among 2000 shades of gray (representing HU values between −1000 and +1000), a radiographer selects a range of CT attenuations that is of interest (e.g., a range of HU values, known as a "window"), and all the CT attenuations within this range are spread over an available gray scale, such as 256 shades of gray. This mapping of a range of CT attenuations to shades of gray is known as windowing. The center of the range is known as the window level. Typically, materials having radio densities higher than the top of the window are depicted in white, whereas materials having radio densities lower than the bottom of the window are depicted in black.

It is difficult to appropriately map images with a large dynamic range with a straight-forward application of the windowing process described above. Currently, operators of an imaging system can adjust the window of an image to view structures within that window only, but cannot simultaneously view multiple windows in a single image. For example, it may be difficult to image bones, organs, and soft tissue in a single image.

BRIEF DESCRIPTION

In one embodiment, a method comprises segmenting an image reconstructed from acquired projection data into segments, converting pixel values based on a mapping for each segment to generate converted segments, and outputting, to a display device, a composite image comprising a combination of the converted segments. The composite image includes a border delineating the converted segments. In this way, multiple windows collectively covering a large dynamic range may be combined into a single image.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
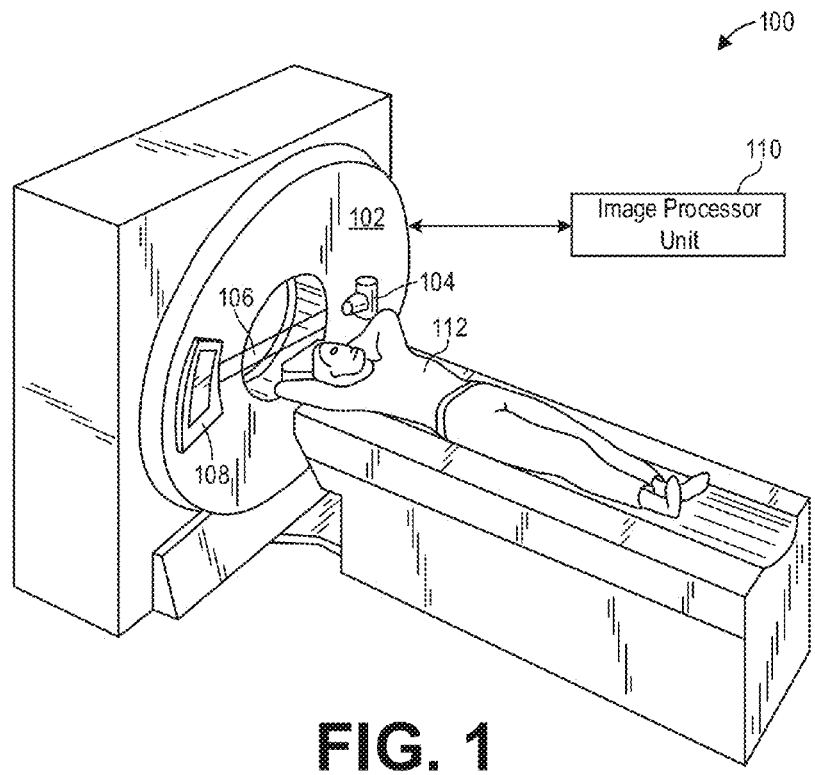
FIG. 1 shows a pictorial view of an imaging system according to an embodiment of the invention.

The following description relates to various embodiments of medical imaging systems. In particular, methods and systems are provided for imaging subjects with a large dynamic range. An example of a computed tomography (CT) imaging system that may be used to acquire images processed in accordance with the present techniques is provided in FIGS. 1 and 2. Known methods for single-window CT imaging assign a gray level to each CT or Hounsfield (HU) number according to a gray level map, such as the linear and non-linear maps depicted in FIGS. 3-4, for images with a small dynamic range (i.e., the structures of interest in the image correspond to CT numbers in a small range wherein a distinct gray level may be assigned to each CT number in the range). Known methods for multi-window imaging convert CT numbers to gray levels using multi-window mapping functions such as the maps depicted in FIGS. 5-6. A method for multi-window imaging, such as the method illustrated in FIGS. 11-12, includes segmenting an image and applying separate gray level maps, such as those depicted in FIGS. 7-10, to the segments.

Though a CT system is described by way of example, it should be understood that the present techniques may also be useful when applied to images acquired using other imaging modalities, such as tomosynthesis, MRI, C-arm angiography, and so forth. The present discussion of a CT imaging modality is provided merely as an example of one suitable imaging modality.

As used herein, the phrase "pixel" also includes embodiments of the invention where the data is represented by a "voxel." Thus, both the terms "pixel" and "voxel" may be used interchangeably herein.

Also as used herein, the phrase "reconstructing an image" is not intended to exclude embodiments of the present invention in which data representing an image is generated, but a viewable image is not. Therefore, as used herein, the term "image" broadly refers to both viewable images and data representing a viewable image. However, many embodiments generate (or are configured to generate) at least one viewable image.

Various embodiments may be implemented in connection with different types of imaging systems. For example, various embodiments may be implemented in connection with a CT imaging system in which an x-ray source projects a fan- or cone-shaped beam that is collimated to lie within an x-y plane of a Cartesian coordinate system and generally referred to as an "imaging plane." The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurement from all the detectors is acquired separately to produce a transmission profile.

In third-generation CT systems, the x-ray source and the detector array are rotated with a gantry within the imaging plane and around the object to be imaged such that the angle at which the x-ray beam intersects the object constantly changes. A complete gantry rotation occurs when the gantry concludes one full 360 degree revolution. A group of x-ray attenuation measurements (e.g., projection data) from the detector array at one gantry angle is referred to as a "view." A view is, therefore, each incremental position of the gantry. A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as a filtered backprojection technique. This process converts the attenuation measurements from a scan into integers called "CT numbers" or "Hounsfield units" (HU), which are used to control the brightness of a corresponding pixel on, for example, a cathode ray tube display.

FIG. 1 illustrates an exemplary CT system 100 configured to allow fast and iterative image reconstruction. Particularly, the CT system 100 is configured to image a subject such as a patient, an inanimate object, one or more manufactured parts, and/or foreign objects such as dental implants, stents, and/or contrast agents present within the body. In one embodiment, the CT system 100 includes a gantry 102, which in turn, may further include at least one x-ray radiation source 104 configured to project a beam of x-ray radiation 106 for use in imaging the patient. Specifically, the radiation source 104 is configured to project the x-rays 106 towards a detector array 108 positioned on the opposite side of the gantry 102. Although FIG. 1 depicts only a single radiation source 104, in certain embodiments, multiple radiation sources may be employed to project a plurality of x-rays 106 for acquiring projection data corresponding to the patient at different energy levels.

In certain embodiments, the CT system 100 further includes an image processing unit 110 configured to reconstruct images of a target volume of the patient using an iterative or analytic image reconstruction method. For example, the image processing unit 110 may use an analytic image reconstruction approach such as filtered backprojection (FBP) to reconstruct images of a target volume of the patient. As another example, the image processing unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the patient.

Figure 2:
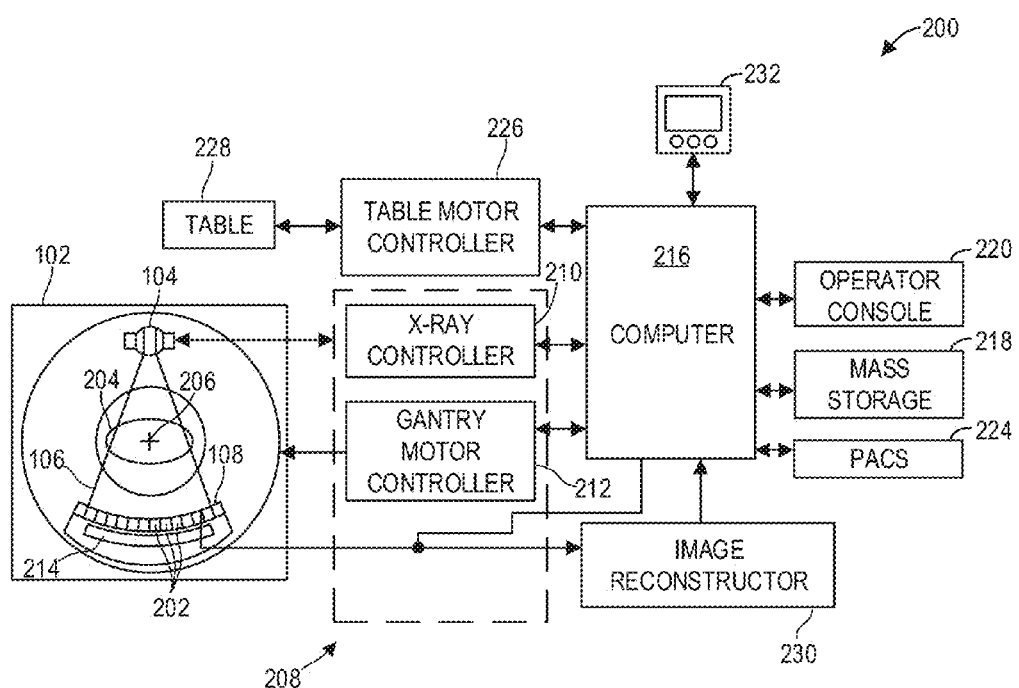
FIG. 2 shows a block schematic diagram of an exemplary imaging system according to an embodiment of the invention.
Figure 3:
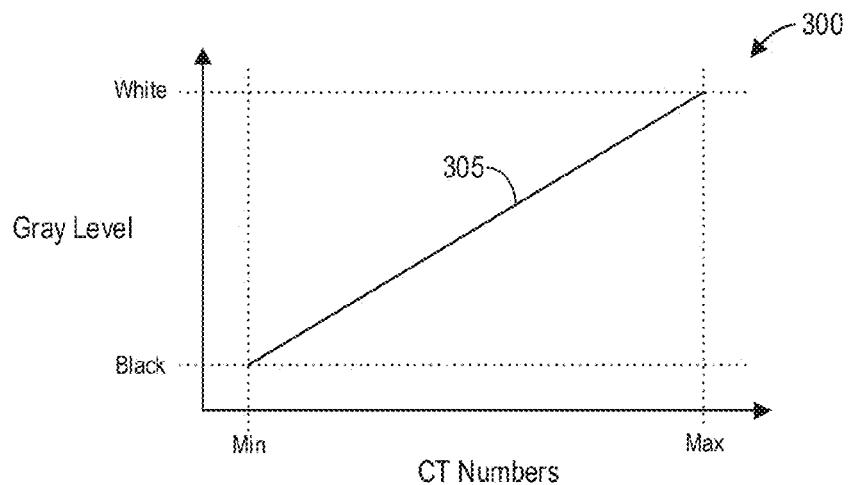
FIGS. 3-6 show graphs illustrating example gray level mapping functions according to the prior art.

FIG. 2 illustrates an exemplary imaging system 200 similar to the CT system 100 of FIG. 1. In accordance with aspects of the present disclosure, the system 200 is configured to reconstruct images with a user-specified temporal window in real-time. In one embodiment, the system 200 includes the detector array 108 (see FIG. 1). The detector array 108 further includes a plurality of detector elements 202 that together sense the x-ray beams 106 (see FIG. 1) that pass through a subject 204 such as a patient to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

In one embodiment, the system 200 includes a control mechanism 208 to control movement of the components such as rotation of the gantry 102 and the operation of the x-ray radiation source 104. In certain embodiments, the control mechanism 208 further includes an x-ray controller 210 configured to provide power and timing signals to the radiation source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The data sampled and digitized by the DAS 214 is transmitted to a computing device 216. In one example, the computing device 216 stores the data in a storage device 218. The storage device 218, for example, may include a hard disk drive, a floppy disk drive, a compact disk-read/write (CD-R/W) drive, a Digital Versatile Disc (DVD) drive, a flash drive, and/or a solid-state storage device.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the system 200, for example, for inputting or outputting system parameters, requesting examinations, and/or viewing images. Further, in certain embodiments, the system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In one embodiment, for example, the system 200 either includes, or is coupled to a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a motorized table 228. Particularly, the table motor controller 226 moves the table 228 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the system 200 and instead the computing device 216 may perform one or more functions of the image reconstructor 230. Moreover, the image reconstructor 230 may be located locally or remotely, and may be operatively connected to the system 100 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 transmits the reconstructed images to the computing device 216 for generating useful patient information for diagnosis and evaluation. In certain embodiments, the computing device 216 transmits the reconstructed images and/or the patient information to a display 232 communicatively coupled to the computing device 216 and/or the image reconstructor 230.

The various methods and processes described further herein may be stored as executable instructions in non-transitory memory on a computing device in system 200. In one embodiment, image reconstructor 230 may include such instructions in non-transitory memory, and may apply the methods described herein to reconstruct an image from scanning data. In another embodiment, computing device 216 may include the instructions in non-transitory memory, and may apply the methods described herein, at least in part, to a reconstructed image after receiving the reconstructed image from image reconstructor 230. In yet another embodiment, the methods and processes described herein may be distributed across image reconstructor 230 and computing device 216.

In one embodiment, the display 232 allows the operator to evaluate the imaged anatomy. The display 232 may also allow the operator to select a volume of interest (VOI) and/or request patient information, for example, via graphical user interface (GUI) for a subsequent scan or processing.

As mentioned above, one method for reconstructing an image from a set of projection data, projection data referring to a group of attenuation measurements, is referred to as the filtered backprojection technique. This process converts the attenuation measurements from a scan into discrete integers, ranging from −1024 to +3072, called "CT numbers" or "Hounsfield units" (HU). For example, an attenuation measurement for air may convert into an integer value of −1000 HU and an attenuation measurement for very dense bone matter may convert into an integer value of +3000 HU, whereas an attenuation measurement for water may convert into an integer value of 0 HU. These HUs are used to control the brightness of a corresponding pixel on a cathode ray tube or a computer screen display in a manner responsive to the attenuation measurements. Specifically, each HU is mapped to a gray level value using a gray level mapping, wherein the HU level of each pixel in an image is converted to a gray level value.

The human eye can distinguish only a limited number of gray levels (roughly 40-100) while the complete diagnostic range of CT numbers may be on the order of 4000 (e.g., from approximately −1000 to +3000, as mentioned above). As a result, mapping the full range of CT numbers to distinct gray level values (ranging from white to black) is undesirable because discrimination between structures with small differences in CT numbers is not possible.

The graphs shown in FIGS. 3-7 illustrate gray level mapping functions known in the prior art. For example, FIG. 3 includes a graph 300 illustrating a linear, monotonic gray level mapping function 305. As depicted in graph 300, the gray level mapping function 305 increases linearly from the minimum CT number (Min), which is set to the lowest gray level (Black), to the maximum CT number (Max), which is set to the highest gray level (White). Each CT number between the minimum and the maximum CT numbers is thus assigned to a distinct gray level value between the minimum (completely black) to the maximum (completely white). The gray level mapping function 305 may be suitable for scenarios with a limited dynamic range, wherein the range of CT numbers (i.e., the window) is small enough to map individual CT numbers in the range (e.g., from Min to Max) to distinct gray level values while reasonably distinguishing structure within the range. Such a limited dynamic range or small window may be on the order of 10 or 100 HU, as a non-limiting example.

Figure 4:
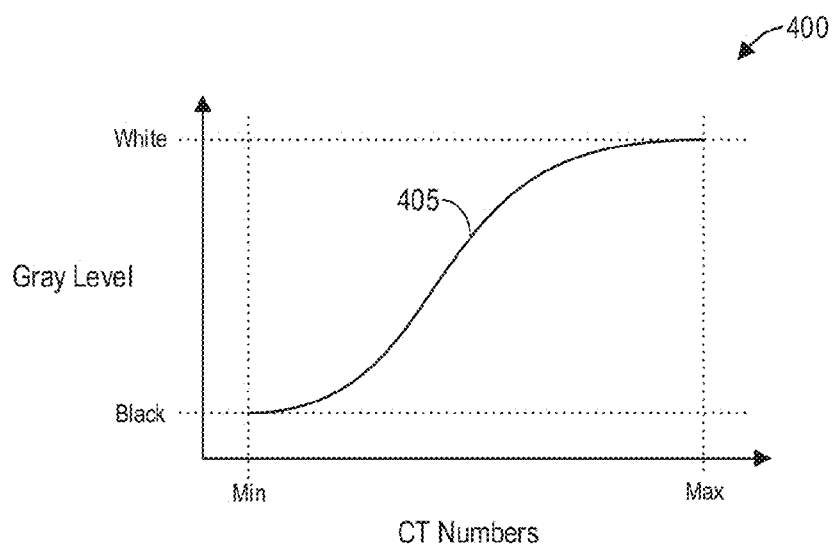

As another example, FIG. 4 includes a graph 400 illustrating a non-linear, monotonic gray level mapping function 405. As depicted, the gray level mapping function 405 extends non-linearly from black to white over a window defined by a minimum CT number and a maximum CT number. Specifically, the gray level mapping function 405 includes curvature such that CT numbers close to the minimum and maximum CT numbers are mapped to gray level values closer, respectively, to black and white gray level values, while CT numbers close to the window center (i.e., the midpoint between the minimum and maximum CT numbers in the window) are mapped to a larger distribution of gray level values with respect to the linear mapping function 305. A non-linear mapping function such as gray level mapping function 405 may be used to resolve additional detail when imaging structures, in comparison to the linear mapping function 305.

Figure 5:
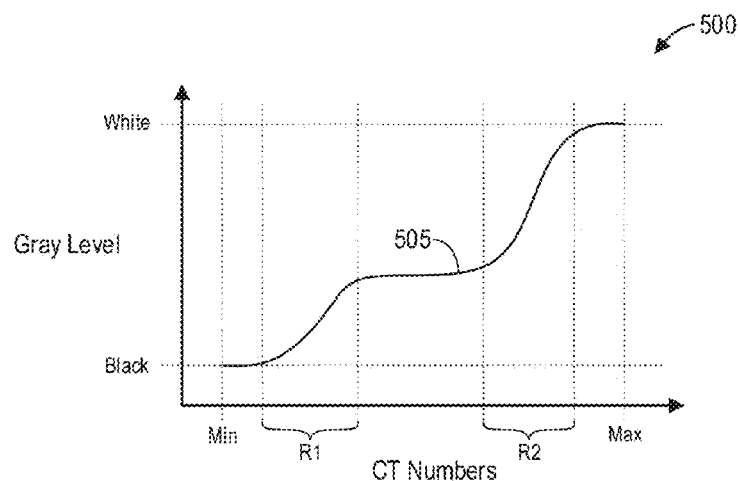

When imaging structures with a larger dynamic range, multiple ranges or windows may be used. The graphs 500 depicted in FIG. 5 illustrates a known approach to multi-window imaging. Specifically, the non-linear, monotonic gray level mapping function 505 includes two ranges or windows R1 and R2 wherein the function 505 increases (i.e., maps CT numbers within the ranges to a distribution of gray level values). Outside of the windows (i.e., between the minimum CT number and the range R1, between the ranges R1 and R2, and between the range R2 and the maximum CT number), the function 505 does not substantially increase. As a result, intermediate structures (i.e., any material represented by a CT number between the two windows) are not resolved.

Figure 6:
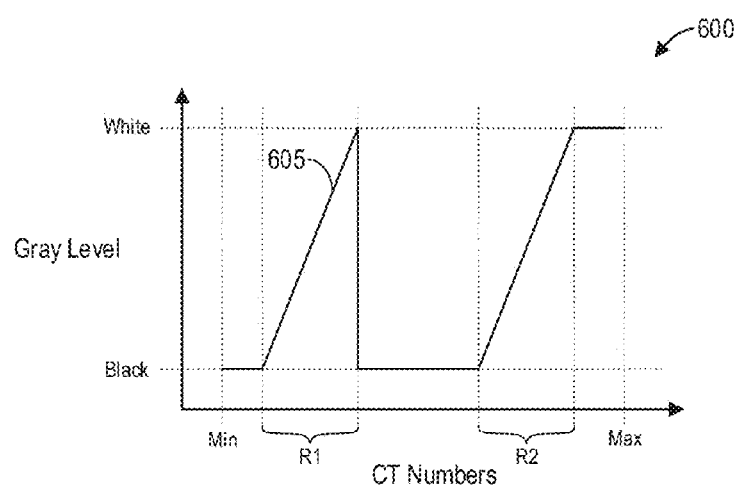

Similarly, FIG. 6 includes a graph 600 illustrating a linear, non-monotonic gray level mapping function 605 with two ranges or windows R1 and R2. The function 605 increases linearly from black to white in both ranges R1 and R2. To that end, the function 605 decreases from white to black at the maximum end of the range R1, such that all intermediate CT numbers between range R1 and range R2 is mapped to black. By duplicating the mapping of different CT numbers to the full range of gray level values, a physician or technician may not be able to distinguish between structures within the range R1 and the range R2. For example, the range R1 may cover soft tissue regions while the range R2 may cover bone, and the function 605 maps CT numbers in both ranges to the same gray values. As a result, the physician or technician may not be able to differentiate between bone and soft tissue.

In order to overcome the limitations of the mapping functions described herein above with regard to FIGS. 3-6, a method for multi-window imaging, such as the method described further herein with regard to FIG. 11, may include segmenting a reconstructed image into segments and applying a mapping function to each segment. The method may use multiple mapping functions, such as those depicted in FIGS. 7-10, to individually map CT numbers to gray level values in different segments of the image. For example, FIG. 7 includes a graph 700 illustrating multiple non-linear, monotonic gray level mapping functions 705 and 710. The gray level mapping function 705 maps CT numbers within a first window or range of CT numbers R1 to the full range of gray level values (e.g., from black to white), while the gray level mapping function 710 maps CT numbers within a second window R2 to the full range of gray level values, wherein the first and second windows R1 and R2 do not overlap. As a result, the two different windows are similarly mapped across the full range of gray level values. Further, the gray level mapping function 705 maps CT numbers above the window R1 to white, while the gray level mapping function 710 maps CT numbers below the window R2 to black.

Figure 8:
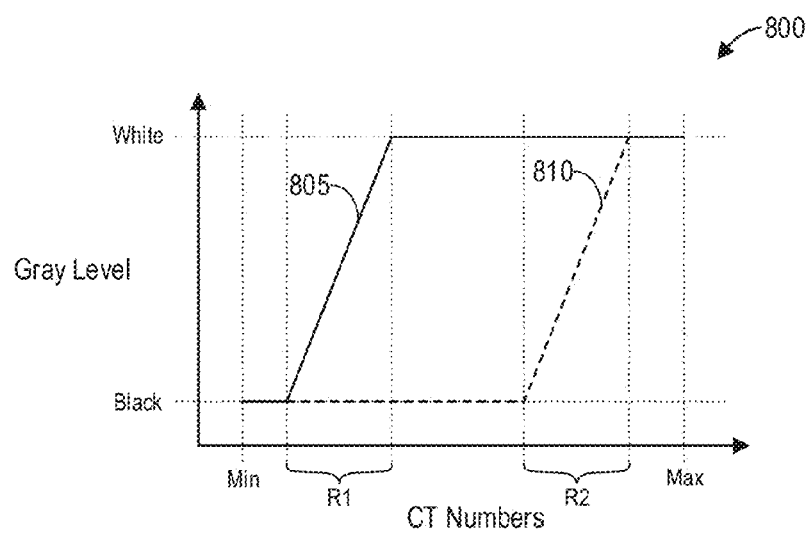
FIG. 8 shows a graph illustrating example linear gray level mapping functions according to an embodiment of the invention.

Similarly, FIG. 8 includes a graph 800 illustrating multiple linear, monotonic gray level mapping functions 805 and 810. The gray level mapping function 805 maps CT numbers within a first window R1 to the full range of gray level values while the gray level mapping function 810 maps CT numbers within a second window R2 to the full range of gray level values. As a result of the linearity of both gray level mapping functions, only CT numbers within window R1 and R2 are mapped to gray level values other than pure black or pure white. As depicted, the mapping function 805 maps CT numbers below the window R1 to black and CT numbers above the window R1 to white, while the mapping function 810 maps CT numbers below the window R2 to black and CT numbers above the window R2 to white.

Figure 7:
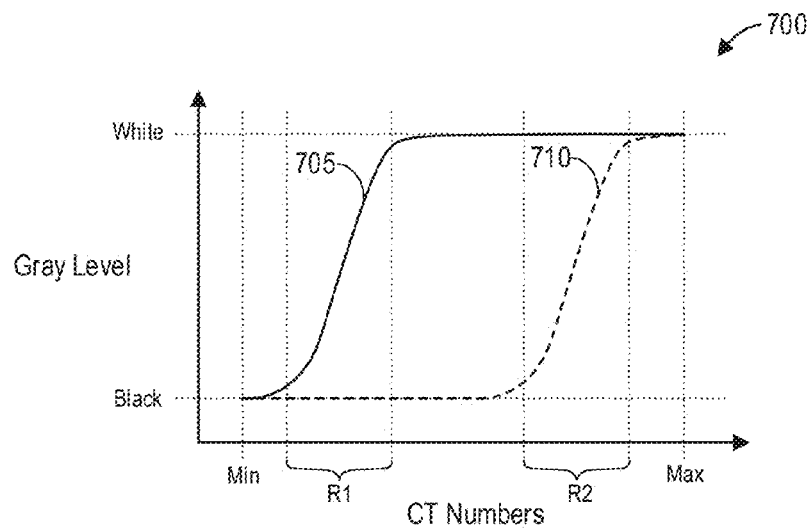
FIG. 7 shows a graph illustrating example non-linear gray level mapping functions according to an embodiment of the invention.

Though the gray level mapping functions depicted in FIGS. 7-8 map CT numbers within non-overlapping ranges of CT numbers, it should be appreciated that in some examples the mapping functions may map overlapping ranges of CT numbers to the distribution of gray level values. For example, FIG. 9 includes a graph 900 illustrating multiple linear, monotonic gray level mapping functions 905 and 910. The gray level mapping function 905 maps CT numbers within a first window R1 to the full range of gray level values while the gray level mapping function 910 maps CT numbers within a second window R2 to the full range of gray level values. Note that the windows R1 and R2 overlap in a segment of intermediate CT numbers. The non-overlapping portion of the window R1 may, as an example, map CT numbers corresponding to an organ (e.g., a lung) while the non-overlapping portion of the window R2 may map CT numbers corresponding to harder material (e.g., bone). Meanwhile, the overlapping portion of the windows R1 and R2 may map soft tissue. In this way, material in the intermediate or overlapping regions, which may include important structures or materials (e.g., a tumor) that may otherwise be ineffectively imaged in the multi-window image, may be effectively imaged. For example, if there is a small section of soft tissue within, say, the lung segment (e.g., the window R1), this small section is not mapped to pure white (effectively segmenting the soft tissue within the lung area out of the lung segment). Instead, the section of soft tissue remains within the lung window and is presented with the lung segment normalization gray level. Thus, this soft tissue (be it a normal part of the lung, or a tumor) is clearly seen against the lung, and this soft tissue, which has the same CT number as soft tissue in the second window, is presented with a different gray level as the corresponding tissue with the same density in the second window.

Similarly, if bone is segmented from the rest of the body (such that the second window corresponds to the bone segment while the first window corresponds to the body segment, or the rest of the material in the body), the bone marrow (within the second window) may have the same CT number level as muscles in the body segment, but the bone marrow and the muscles are presented with different gray levels, each in its corresponding zone or segment. In this way, segmentation may be organ-oriented, and after the segmentation, each segment or zone is separately normalized.

Furthermore, though two gray level mapping functions are described herein above, it should be appreciated that a number of mapping functions greater than two may be used. For example, FIG. 10 includes a graph 1000 illustrating multiple linear, monotonic gray level mapping functions 1005, 1007, and 1010. The gray level mapping function 1005 maps CT numbers within a first window R1 to the distribution of gray level values, the gray level mapping function 1007 maps CT numbers within a second window R2 to the distribution of gray level values, and the gray level mapping function 1010 maps CT numbers within a third window R3 to the distribution of gray level values. Though the windows R1, R2, and R3 are depicted as non-overlapping, in some examples the windows may overlap as described above. As a non-limiting example, the windows may be selected such that the first window R1 images a lung, the second window R2 images soft tissue, and the third window R3 images bone (ranging from bone marrow to hard bone).

Figure 9:
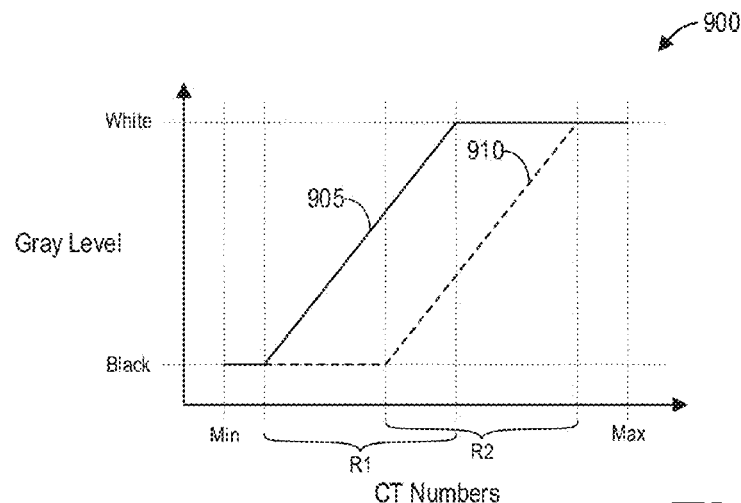
FIG. 9 shows a graph illustrating example linear and overlapping gray level mapping functions according to an embodiment of the invention.
Figure 10:
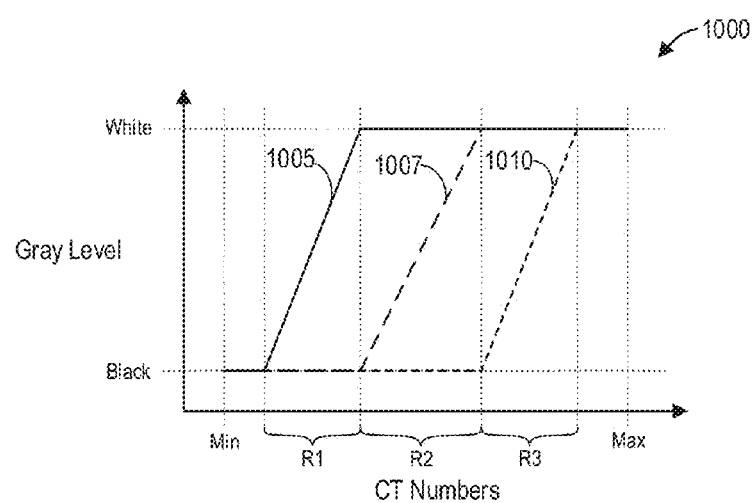
FIG. 10 shows a graph illustrating three linear and non-overlapping gray level mapping functions according to an embodiment of the invention.

Further, although the mapping functions of FIG. 7 are both non-linear and the mapping functions of FIGS. 8-10 are linear, in some examples a combination of non-linear and linear mapping functions may be used to map CT numbers to gray level values in a single image. Furthermore, while gray level is described for simplicity, in some examples different mapping functions may map CT numbers to different values in a color channel (e.g., red, green, or blue in an RGB image; cyan, magenta, yellow, or black in a CMYK image, and so on).

In some examples, the systems, methods, and devices in accordance with this disclosure may include a plurality of settings for an operator to select when generating an image. For example, when the imaging apparatus is in a first setting, the imaging apparatus may use the method of multi-window imaging described herein with non-overlapping mapping functions, and when the imaging apparatus is in a second setting, the imaging apparatus may use the method with overlapping mapping functions. Both the first setting and the second setting may be separately used to generate an image from the same projection data. Similarly, as non-limiting examples, the imaging apparatus may include settings that allow an operator to: select the color channels for each mapping function (e.g., gray, blue, green, red, and so on); select linear mapping functions, non-linear mapping functions, or a combination thereof; and selectively adjust the curvature of one or more mapping functions.

Figure 11:
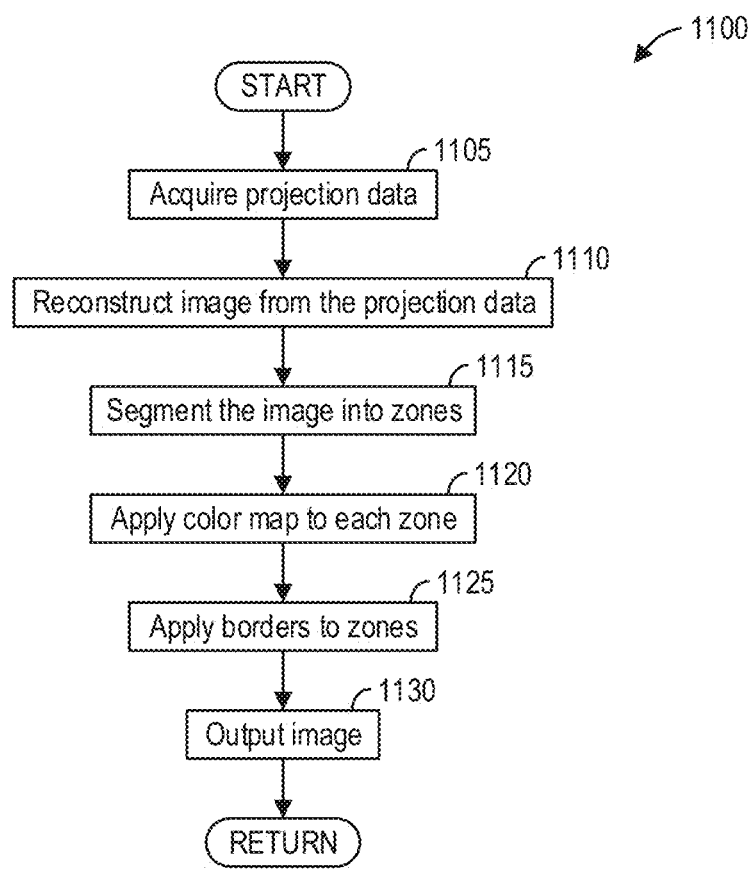
FIG. 11 shows a high-level flow chart illustrating an example method for multi-window imaging according to an embodiment of the invention.

FIG. 11 shows a high-level flow chart illustrating an example method 1100 for multi-window imaging according to an embodiment. In particular, method 1100 relates to segmenting a reconstructed image into segments and applying mappings to each segment. Method 1100 may be carried out by the components and systems depicted in FIGS. 1 and 2, however it should be understood that the method may be implemented on other components and systems not depicted without departing from the scope of the present disclosure. As an example, method 1100 may be implemented as executable instructions in non-transitory memory that when executed cause a computer to perform the actions described herein. For example, the method may be stored as instructions in non-transitory memory, such as the non-transitory memory of computer 216 and/or image reconstructor 230, the instructions executable by a computer such as the computer 216 and/or the image reconstructor 230.

Method 1100 may begin at 1105. At 1105, method 1100 acquires projection data. Acquiring projection data comprises scanning a subject, such as a patient, using an imaging system such as the system described herein with regard to FIGS. 1-2. After acquiring the projection data, at 1110, method 1100 reconstructs an image from the projection data.

At 1115, method 1100 segments the image into zones. In some examples, the method segments the image using a simple threshold technique such that each zone of the image corresponds to a particular range of CT numbers. Preferably, the zones do not overlap. When imaging organs, preferably the method segments the image along organ boundaries. To that end, in one example the method may use an atlas to identify organs and organ boundaries. In another example, the method segments the image along organ boundaries responsive to user input. For example, a user may manually identify organs within the image via, as a non-limiting example, operator console 220. In yet another example, in hybrid nuclear medicine (NM)-CT imaging, organ identification is NM-assisted or NM-oriented. For example, organs may be automatically identified in a positron emission tomography (PET) image more easily than a CT image, and the CT image may be segmented based on the automatic organ identification in the PET image. Thus, the image may be registered and/or fused with images acquired using other modalities, including but not limited to MRI, SPECT, and so on. Additionally, the segmentation applied to the CT image may be further used to segment the registered image of the other modality, and this co-segmentation may be used for applying, to the non-CT image or images acquired using the other modality, different gray level mapping functions to the segments of the non-CT image as described further herein. Even further, the method may utilize a look-up table to draw or depict fused parts of multi-modality images for specific segments.

After segmenting the image into segments or zones, at 1120, method 1100 applies a mapping function to the pixels or voxels in each zone. In some examples, a separate mapping function may be applied to each zone. A mapping function applied to a segment converts the value of each pixel in the segment into a gray level value based on the CT number of the pixel. In some examples, the particular mapping function applied to a zone is based on characteristics of the zone, for example the mapping function may be defined based on the window width of the zone (i.e., the range of CT numbers within the segment). Further, if the zone contains specific types of structures, a mapping function applied to the zone may be selected or defined to optimally resolve structural details within the zone. In this way, the different zones may be separately normalized according to the mapping functions.

In some examples, the mapping functions may comprise color value mapping functions. For example, a color value mapping function may map CT numbers to color values in a particular color channel (e.g., one of an RGB channel such as a red, green, or blue channel). Different zones may be mapped to different color channels. As a non-limiting example, a zone or segment containing bone may be mapped to a blue channel (so that CT numbers are mapped to varying levels of blue) while a segment containing soft tissue is mapped to a red channel (so that CT numbers are mapped to varying levels of red).

At 1125, method 1100 applies borders to the boundaries of the zones or segments. In some examples, the borders may be colored to visually distinguish the border from the rest of the image. For example, the borders may be green or red to differentiate the border from a grayscale CT image. The color of the border may be automatically selected based on an analysis of the image. If the CT image is colorized, the color of the border may be automatically or manually selected to distinguish the border from the color of surrounding anatomical structures.

At 1130, method 1100 outputs the image. The image may be output to, as non-limiting examples, a display device (e.g., display device 232) for display to a physician or technician, to a storage medium (e.g., mass storage 218) for later retrieval, and so on. When displayed on a display device, a physician or technician may view the image comprising separately mapped segments with a border demarking the boundaries of the segments. Method 1100 then ends.

Figure 12:
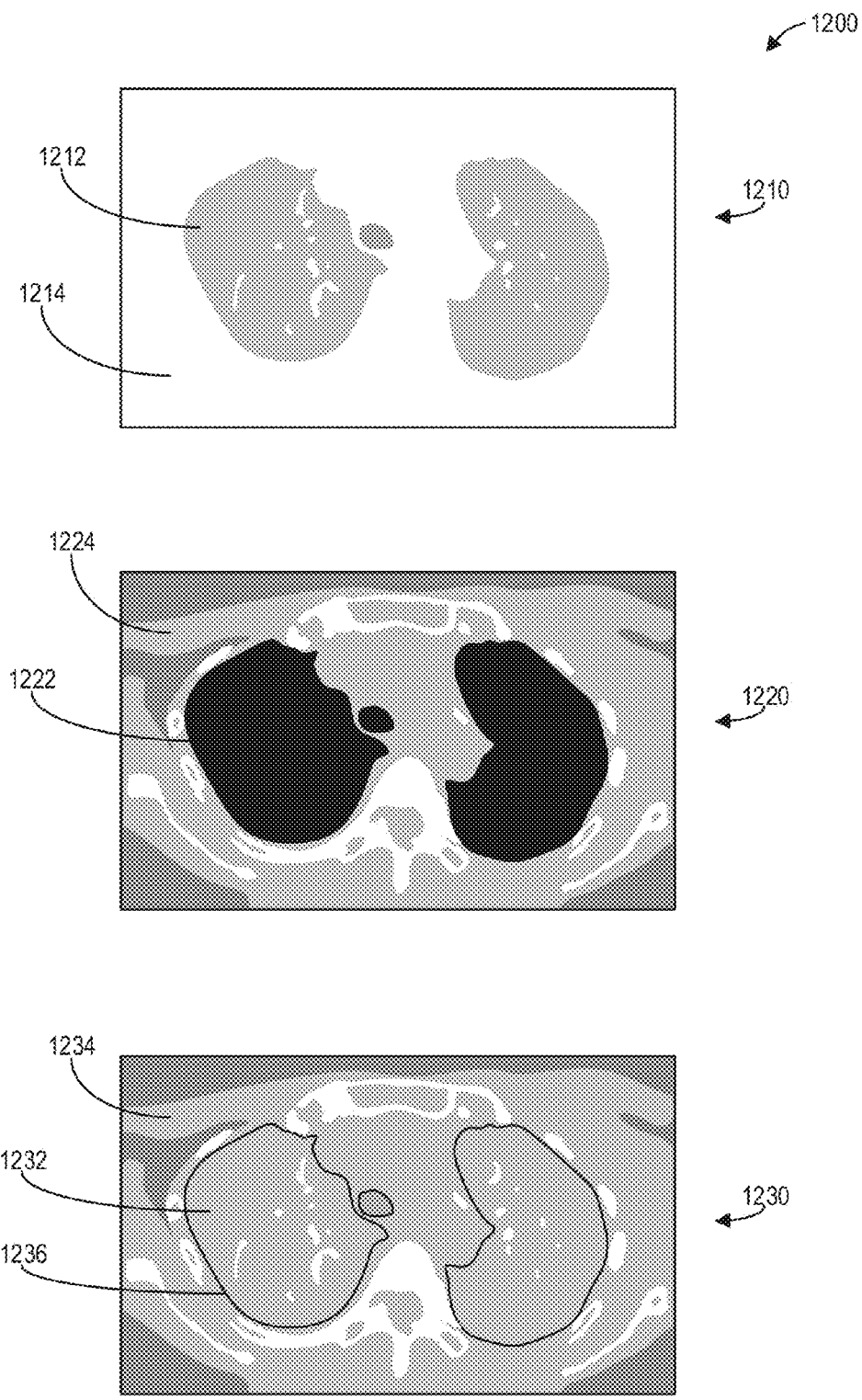
FIG. 12 shows a set of images illustrating a method for multi-window imaging according to an embodiment of the invention.

FIG. 12 includes a set of images 1200 illustrating, in part, a method for multi-window imaging, such as the method 1100 described herein above with regard to FIG. 11. The set of images 1200 comprise example images reconstructed in the axial plane from projection data acquired when scanning the lungs of a patient.

The lung image 1210 comprises an image reconstructed with lung window settings, wherein the lung window includes CT numbers typical to organs. The lungs 1212 appear as gray, while the surrounding anatomy 1214 appears entirely as white since the surrounding anatomy 1214 corresponds to material with CT numbers above the CT numbers comprising the lung window.

Meanwhile, the soft tissue image 1220 comprises an image reconstructed with soft tissue window settings, wherein the soft tissue window includes CT numbers typical to soft tissue. In the soft tissue image 1220, the lungs 1222 appear entirely as black since the CT numbers corresponding to the lungs are below the CT numbers comprising the soft tissue window, and the surrounding anatomy 1224 (i.e., the soft tissue) is resolved in various shades of gray based on CT number.

Typically, a radiologist or physician would select an appropriate window (e.g., lung window, soft tissue window) to view the desired anatomy (e.g., the lungs, the soft tissue surrounding the lungs), but could not simultaneously view both windows in a single image without confusion. The composite image 1230 comprises a combination of the lungs image 1210 and the soft tissue image 1220. Specifically, the composite image 1230 includes an image of the lungs 1232 comprising the image of the lungs 1212 in the lung image 1210. The composite image 1230 further includes the soft tissue 1234 comprising the image of the soft tissue 1224 in the soft tissue image 1220. To mitigate confusion regarding similar gray levels in both segments of the composite image 1230, the composite image 1230 further includes a border 1236 that visually defines the boundary between the soft tissue 1234 and the lungs 1232. In this way, a physician or technician viewing the composite image 1230 may easily understand that a gray value seen within the soft tissue 1234 corresponds to a different CT number than the same gray value seen within the lungs 1232.

To generate the composite image 1230, a method may segment an image (e.g., lung image 1210) into different zones or segments (e.g., a lung segment 1212 and a soft tissue segment 1214), apply a mapping function to each segment (e.g., a lung window to the lung segment and a soft tissue window to the soft tissue segment) to convert CT numbers of each segment into corresponding gray level values, combine the converted segments (e.g., lungs 1212 and soft tissue 1224) into the composite image 1230, and apply a border 1236 to the segment boundaries. In this way, multiple windows may be displayed in a single image.

A technical effect of the disclosure includes the generation and displaying of an image comprising multiple windows with a border therebetween. Another technical effect of the disclosure includes the mapping of different ranges of CT numbers to a same brightness scale. Yet another technical effect of the disclosure includes the reconstruction of an image from projection data with a large dynamic range.

Various systems and methods for multi-window imaging are provided. In one embodiment, a method comprises segmenting an image reconstructed from acquired projection data into segments, converting pixel values based on a mapping for each segment to generate converted segments, and outputting, to a display device, a composite image comprising a combination of the converted segments. In a first example of the method, the method further comprises applying a border to boundaries of the converted segments in the composite image. In a second example of the method optionally including the first example, the mapping comprises a function that maps the pixel values from Hounsfield units to gray level values. In a third example of the method optionally including one or more of the first and second examples, the mapping comprises a function that maps the pixel values from Hounsfield units to color channel values, wherein different color channels are used for each segment. In a fourth example of the method optionally including one or more of the first through third examples, segmenting the image comprises segmenting along organ boundaries in the image based on an atlas. In a fifth example of the method optionally including one or more of the first through fourth examples, segmenting the image comprises segmenting along organ boundaries in the image responsive to user input. In a sixth example of the method optionally including one or more of the first through fifth examples, segmenting the image comprises segmenting the image along organ boundaries identified in a corresponding and co-registered nuclear medicine image. In a seventh example of the method optionally including one or more of the first through sixth examples, the mapping comprises a linear mapping. In an eighth example of the method optionally including one or more of the first through seventh examples, the mapping comprises a non-linear mapping. In a ninth example of the method optionally including one or more of the first through eighth examples, the method further comprises adjusting the mapping responsive to user input. In a tenth example of the method optionally including one or more of the first through ninth examples, the method further comprises selecting a color of the border based on the composite image, wherein the color of the border complements colors of the composite image. In an eleventh example of the method optionally including one or more of the first through tenth examples, the mapping applied to each segment is selected based on contents of that segment.

In another embodiment, a non-transitory computer-readable storage medium includes executable instructions stored thereon that when executed by a computer cause the computer to: reconstruct an image based on acquired projection data; segment the image into at least two segments; select at least a first mapping and a second mapping respectively for a first segment and a second segment of the at least two segments; convert the first segment based on the first mapping and the second segment based on the second mapping; and generate, for display via a display device, a composite image comprising the converted first segment, the converted second segment, and a border between the converted first segment and the converted second segment. In a first example of the non-transitory computer-readable storage medium, the first mapping maps a first range of Hounsfield units in the first segment to a gray scale and the second mapping maps a second range of Hounsfield units in the second segment to the gray scale, wherein the first range and the second range do not overlap. In a second example of the non-transitory computer-readable storage medium optionally including the first example, the executable instructions further cause the computer to adjust at least one of the segmentation of the image, the first mapping, the second mapping, and a color of the border responsive to and based on user input. In a third example of the non-transitory computer-readable storage medium optionally including one or more of the first and second examples, the first mapping maps a first range of Hounsfield units in the first segment to a first color channel scale and the second mapping maps a second range of Hounsfield units in the second segment to a second color channel scale, wherein the first range and the second range do not overlap.

In yet another embodiment, a system comprises: an x-ray source that emits a beam of x-rays toward an object to be imaged; a detector that receives the x-rays attenuated by the object; a data acquisition system (DAS) operably connected to the detector; and a computer operably connected to the DAS and configured with instructions in non-transitory memory that when executed cause the computer to: reconstruct an image based on projection data acquired via the DAS; segment the image into a first segment and a second segment; convert pixel values of the first segment and the second segment based on a first mapping and a second mapping respectively; and generate a composite image comprising the converted first segment, the converted second segment, and a border between the converted first segment and the converted second segment. In a first example of the system, the system further comprises a display device, and the instructions further cause the computer to output the composite image to the display device. In a second example of the system optionally including the first example, the first mapping maps a first range of Hounsfield units to a gray scale and the second mapping maps a second range of Hounsfield units to the gray scale, wherein the first range and the second range do not overlap. In a third example of the system optionally including one or more of the first and second examples, the image is segmented along organ boundaries based on an atlas.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
    acquiring projection data via a detector;
    segmenting a two-dimensional image reconstructed from the acquired projection data into segments;
    generating converted segments based on a mapping for each segment, wherein the mapping for each segment is different, and each mapping maps pixel values of the segment to a range of different values of corresponding converted segment; and
    outputting, to a display device, a composite image comprising a combination of the converted segments.

2. The method of claim 1, further comprising applying a border to boundaries of the converted segments in the composite image.

3. The method of claim 2, further comprising selecting a color of the border based on the composite image, wherein the color of the border complements colors of the composite image.

4. The method of claim 1, wherein the mapping for each segment comprises a function that maps the pixel values of each segment from Hounsfield units to a full range of gray level values.

5. The method of claim 1, wherein the mapping for each segment comprises a function that maps the pixel values of each segment from Hounsfield units to different values in a color channel, wherein different color channels are used for each segment.

6. The method of claim 1, wherein segmenting the two-dimensional image comprises segmenting along organ boundaries in the two-dimensional image based on an atlas.

7. The method of claim 1, wherein segmenting the two-dimensional image comprises segmenting along organ boundaries in the two-dimensional image responsive to user input.

8. The method of claim 1, wherein segmenting the two-dimensional image comprises segmenting the two-dimensional image along organ boundaries identified in a corresponding and co-registered nuclear medicine image.

9. The method of claim 1, wherein the mapping for each segment comprises a linear mapping.

10. The method of claim 1, wherein the mapping for each segment comprises a non-linear mapping.

11. The method of claim 1, further comprising adjusting the mapping for each segment responsive to user input.

12. The method of claim 1, wherein the mapping applied to each segment is selected based on contents of that segment.

13. A non-transitory computer-readable storage medium including executable instructions stored thereon that when executed by a computer cause the computer to:
    acquire projection data via a detector;
    reconstruct an image based on the acquired projection data;
    segment the image into at least two segments;
    select at least a first mapping and a second mapping respectively for a first segment and a second segment of the at least two segments;
    convert the first segment based on the first mapping and the second segment based on the second mapping, wherein the first mapping maps a range of pixel values of the image to a first range of pixel values of the first converted segment, the second mapping maps the range of pixel values of the image to a second range of pixel values of the second converted segment, the second range different from the first range; and
    generate, for display via a display device, a composite image comprising the converted first segment, the converted second segment, and a border between the converted first segment and the converted second segment.

14. The non-transitory computer-readable storage medium of claim 13, wherein the pixel values of the image are Hounsfield units, and the first mapping further maps a first range of Hounsfield units in the first segment to a gray scale and the second mapping maps a second range of Hounsfield units in the second segment to the gray scale, the first range of Hounsfield units different from the second range of Hounsfield units.

15. The non-transitory computer-readable storage medium of claim 13, wherein the executable instructions further cause the computer to adjust at least one of the segmentation of the image, the first mapping, the second mapping, and a color of the border responsive to and based on user input.

16. The non-transitory computer-readable storage medium of claim 13, wherein the first mapping maps a first range of Hounsfield units in the first segment to different values in a first color channel and the second mapping maps a second range of Hounsfield units in the second segment to different values in a second color channel.

17. A system, comprising:
an x-ray source that emits a beam of x-rays toward an object to be imaged;
a detector that receives the x-rays attenuated by the object;
a data acquisition system (DAS) operably connected to the detector; and
a computer operably connected to the DAS and configured with instructions in non-transitory memory that when executed cause the computer to:
reconstruct a two-dimensional image based on projection data acquired via the DAS;
segment the two-dimensional image into a first segment and a second segment;
generating converted segments by converting pixel values of the first segment and the second segment based on a first mapping and a second mapping respectively, the first mapping different from the second mapping, and wherein each mapping maps pixel values of the segment to a range of different values of corresponding converted segment; and
generate a composite image comprising a converted first segment, a converted second segment, and a border between the converted first segment and the converted second segment.

18. The system of claim 17, further comprising a display device, and wherein the instructions further cause the computer to output the composite image to the display device.

19. The system of claim 17, wherein the first mapping maps a first range of Hounsfield units to a gray scale and the second mapping maps a second range of Hounsfield units to the gray scale, wherein the first range and the second range do not overlap.

20. The system of claim 17, wherein the first mapping maps a first range of Hounsfield units to a gray scale and the second mapping maps a second range of Hounsfield units to the gray scale, wherein the first range and the second range overlap.

* * * * *